United States Patent [19]

Kitajima et al.

[11] 4,340,565
[45] Jul. 20, 1982

[54] HEMATOCRIT VALUE DETERMINING ELEMENT

[75] Inventors: Masao Kitajima; Fuminori Arai; Asaji Kondo, all of Asaka, Japan

[73] Assignee: Fuji Photo Film Co., Ltd., Kanagawa, Japan

[21] Appl. No.: 221,183

[22] Filed: Dec. 29, 1980

[30] Foreign Application Priority Data

Dec. 28, 1979 [JP] Japan .............................. 54-173624

[51] Int. Cl.³ ...................... G01N 33/50; G01N 33/52
[52] U.S. Cl. .................................... 422/56; 23/230 B; 422/55
[58] Field of Search ............................. 422/56, 55, 58; 23/230 B

[56] References Cited

U.S. PATENT DOCUMENTS

| | | | |
|---|---|---|---|
| 3,990,849 | 11/1976 | Lee | 23/230 B |
| 3,992,158 | 11/1976 | Przybylowicz | 422/58 X |
| 4,144,306 | 3/1979 | Figueras | 422/56 |
| 4,160,008 | 7/1979 | Fenocketti | 422/56 |
| 4,166,093 | 8/1979 | Smith-Lewis | 422/56 |
| 4,250,257 | 2/1981 | Lee | 422/56 X |
| 4,260,392 | 4/1981 | Lee | 422/58 X |

*Primary Examiner*—Sidney Marantz
*Attorney, Agent, or Firm*—Sughrue, Mion, Zinn, Macpeak & Seas

[57] ABSTRACT

A hematocrit value determining element comprising, in one embodiment, a water-impermeable planar support having integrally provided thereon a hydrophilic porous spreading layer, the porous spreading layer being such that blood spreads therethrough depending upon the viscosity of the blood and, in a second embodiment, a hematocrit value determining element as described above and a binder layer provided between the planar support and the porous spreading layer.

17 Claims, 5 Drawing Figures

HEMATOCRIT VALUE DETERMINING ELEMENT

FIELD OF THE INVENTION

This invention relates to a layered, integral material for determining hematocrit value of blood which is an important test item in the field of medical, clinical or physiological hematology.

BACKGROUND OF THE INVENTION

As is well known, blood is composed of plasma and cell ingredients (i.e., erythrocytes, leukocytes, thrombocytes, etc.). The volume percentage of erythrocytes based on the volume of whole blood is called the hematocrit value, which is an important value to know in assessing the degree of anemia. Methods for determining the hematocrit value (hereinafter abbreviated as "HCT") that have so far been utilized include a centrifuging method, an electrical resistance method, a specific gravity-measuring method, etc. However, these methods have the defects that a long time and complicated wet procedures are required to conduct these methods.

SUMMARY OF THE INVENTION

An object of the present invention is to provide a simple and dry HCT-determining material which enables HCT to be determined through a procedure of only applying thereto one drop of an extremely small amount of whole blood.

The present invention comprises in one embodiment an integral hematocrit value determining material comprising a water-impermeable planar support having integrally provided thereon a porous spreading layer which has a hydrophilic surface and in which the surface of the internal voids or the interior is hydrophilic and water-insoluble (such being hereinafter simply referred to as "hydrophilic"), the porous spreading layer being such that blood can be spread therethrough depending upon the spreading nature, e.g., viscosity of the blood; and in a second embodiment a hematocrit value determining material as described above and additionally including a binder layer between the support and the porous spreading layer.

BRIEF DESCRIPTION OF THE DRAWINGS

In FIGS. 1 through 4, reference numeral 1 designates a water-impermeable planar support, 2 a binder, 3 a hydrophilic porous spreading layer, 5 an inside spread circle, 6 an outside spread circle, 7 the diameter of the outside spread circle, 8 the diameter of the inside spread circle, A the direction of applying the blood sample and viewing and measuring the spread circles from the porous spreading layer side, and B the direction of viewing and measuring the spread circles from the support side when using a transparent water-impermeable planar support.

DETAILED DESCRIPTION OF THE INVENTION

Figure 1:
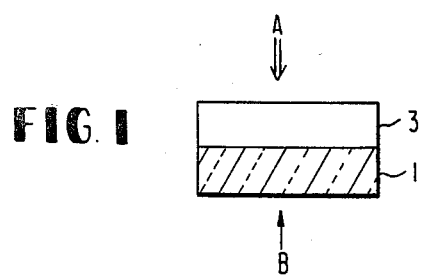
FIG. 1 is a schematic sectional view showing one embodiment of an HCT-determining material comprising a water-impermeable planar support having integrally provided thereon a hydrophilic porous spreading layer.
Figure 2:
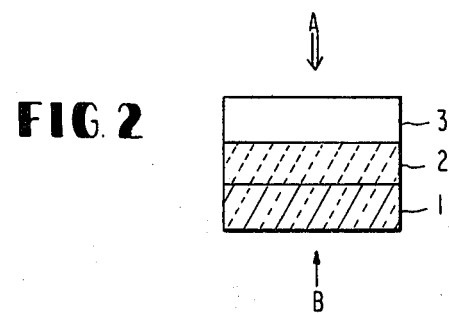
FIG. 2 is a schematic sectional view showing one embodiment of an HCT-determining material comprising a water-impermeable planar support having provided thereon, in sequence, a binder layer and a hydrophilic porous layer.

The present invention will be described by reference to HCT-determining sheets shown in the attached drawings, which are embodiments of the present invention. The HCT-determining sheet of the present invention has a fundamental structure as shown in FIG. 1 wherein a porous spreading layer 3 is provided on a water-impermeable support 1 to form an integral sheet, or has a fundamental structure as shown in FIG. 2 wherein a binder layer 2 and a porous spreading layer 3 are provided on a hydrophobic planar support 1 to form an integral sheet. The binder layer 2 is not a necessary constituent of the present invention but, in a usual production process, it is preferably used to adhere the hydrophobic support 1 to the porous spreading layer 3 in a fluid contact state, which state is defined in U.S. Pat. Nos. 3,922,158 and 4,042,335 and U.S. Pat. No. Re. 30,267.

Figure 3:
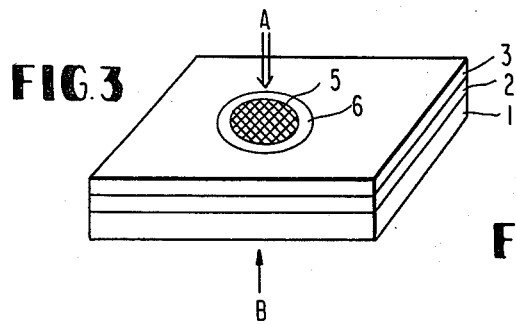
FIG. 3 is a perspective view showing a spread blood sample applied to a porous spreading layer of an HCT-determining sheet schematically shown in FIG. 2.

In determining HCT, a drop of whole blood is applied to the HCT-determining sheet of the present invention from side A of the porous spreading layer as shown in FIG. 3 showing a perspective view of the sheet. The amount of whole blood to be applied thereto is suitably between about 5 and 100 $\mu l$, for example 10 $\mu l$. The thus applied whole blood immediately spreads into the hydrophilic, porous spreading layer concentrically in a horizontal direction to form a colored concentric inside circle 5 containing erythrocytes and a less colored concentric outside circle 6 within several tens of seconds. As a result the spreading of a sample is completed.

Figure 4:
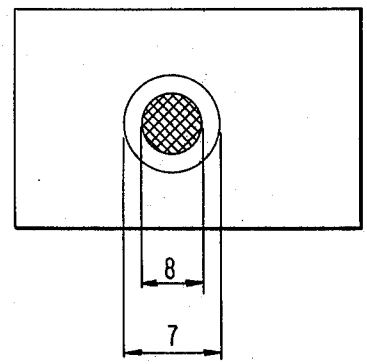
FIG. 4 is a schematic view showing the state wherein a blood sample is spread through the porous spreading layer of the HCT-determining sheet shown in FIG. 1.

The HCT can be determined by measuring the diameter of the spread outside circle 7 or both the diameter of the spread outside circle and that of the spread inside circle 8 as shown in FIG. 4 from the direction indicated by arrow A or B, and referring to a previously prepared conversion table or calibration.

The spreading layer for the HCT-determining sheet of the present invention can be a fibrous or non-fibrous porous membrane having a hydrophilic and water-insoluble surface and having internal voids whose surface is hydrophilic and water-insoluble or having a hydrophilic and water-insoluble interior. The desired degree of porosity varies depending upon the degree of hydrophilicity, state of pores, form and distribution of pores, etc. and it is difficult to set forth specific ranges. By way of general guidance, however, where the spreading layer comprises a non-fibrous porous material, the mean pore diameter can range from about 0.1 $\mu m$ to about 2.5 $\mu m$, preferably from about 0.4 $\mu m$ to about 2 $\mu m$ and, where the spreading layer comprises a fibrous porous material like a fabric (broad cloth), fabrics formed using two folded yarns with a yarn number count of about 100 to about 200, preferably from about 120 to about 160, are used. A suitable degree of porosity ranges from about 20 to about 80%, preferably from about 25 to about 80%.

Examples of suitable hydrophilic porous spreading layers which can be used include non-fibrous porous membranes as disclosed in U.S. Pat. Nos. 3,553,067, 3,594,263, 3,922,158, 4,050,898, etc., those prepared by rendering hydrophilic non-fibrous porous membranes, porous particulate membranes, fabrics rendered hydrophilic described in Japanese patent application Ser. No. 72,047/79 corresponding to U.S. patent application Ser. No. 157,737, filed June 9, 1980, sheets composed of glass fibers or papers, etc. Exemplary fabrics which can be used may be knitted or woven, and suitable examples of fabrics which can be used include fabrics composed of natural fibers, fabrics of mixed yarns or natural fibers and synthetic polymers, and fabrics composed of synthetic polymers. Of these, membrane filters having the characteristics described hereinafter are particularly preferred. When using such membrane filters, those with a pore size of from about 0.1 $\mu$m to about 3 $\mu$m can be used, with a pore size of from about 0.4 $\mu$m to about 2 $\mu$m being preferred.

The thickness of the porous spreading layer is not particularly limited as long as the thickness is not less than about 10 $\mu$m but, in view of the amount of liquid applied, measurement accuracy, handling properties, etc., the thickness generally ranges of from about 30 $\mu$m to about 3 mm, preferably from about 50 $\mu$m to about 1 mm, more preferably from 100 $\mu$m to 500 $\mu$m.

The porous spreading layer used in the present invention may have a uniform structure composed of a single material, or may be formed by combining two or more materials having different physical properties so as to obtain improved properties.

Suitable processes for integrally providing a porous spreading layer on a water-impermeable planar support or on a binder layer, include integrally laminating a previously prepared porous membrane or fabric on the support or the binder layer, and coating a solution or dispersion capable of forming a porous spreading layer on the support or the binder layer to thereby integrally form a porous spreading layer, both processes being properly utilized.

The porous spreading layer to be used for the hematocrit value determining sheet of the present invention must possess properties such that the surface to which the sample is to be applied and the surface of voids in the porous spreading layer or the interior thereof have high hydrophilicity and that, when applying a drop of blood thereto, the blood spreads almost isotropically within the plane to which the blood is applied. In order to obtain such properties, the porous materials must be subjected to a treatment to render such hydrophilic. Suitable treatments which can be used are a surface treatment using a hydrophilic compound such as a cationic, anionic, or nonionic surfactant or a plasticizer, or a colloid (e.g., gelatin), a treatment to render such hydrophilic by, for example, hydrolysis with an acid or an alkali, a treatment of chemically rendering such hydrophilic by reaction with a hydrophilic compound, a corona treatment, a flame treatment, an ultraviolet light irradiation treatment, an electric discharge treatment, a vacuum deposition treatment, a spraying treatment, etc.

Addition of agents for stabilizing the hue of hemoglobin, such as a pH buffer, an anticoagulant, an antihemolytic agent, an antioxidant, an oxidizing agent, etc., and erythrocyte membrane-modifying agents such as a dye, a pigment, an inorganic salt, an aldehyde, an isocyanate, hydrogen peroxide, etc. to the porous spreading layer serves to improve accuracy or improve procedures like readout.

Suitable water-impermeable planar support materials which can be used to form the HCT-determining sheet of the present invention include plate-like materials of metal, wood, paper, glass, or the like, a synthetic resin film such as of polyester (e.g., polyethylene terephthalate, bisphenol A polycarbonate, etc.), cellulose ester (e.g., cellulose diacetate, cellulose triacetate, cellulose acetate propionate, etc.) or polymethyl methacrylate, or the like. The thickness of the water-impermeable planar support ranges from about 10 $\mu$m to about 3 mm, preferably from about 20 $\mu$m to about 1 mm, most preferably from about 50 $\mu$m to about 500 $\mu$m. Of these, transparent planar supports are convenient because they permit the diameter of the spread circle to be measured from either side of the HCT-determining sheet.

The HCT-determining sheet of the present invention comprising a water-impermeable planar support having integrally provided thereon a hydrophilic porous spreading layer may contain a binder layer which functions to uniformly adhere the porous spreading layer to the support in a fluid contact state and to control the spreading of a blood sample through the porous spreading layer within a suitable range.

A hydrophobic binder may be used for the binder layer as long as it does not completely repel water, but, for determining HCT with high accuracy, it is desirable to primarily use a hydrophilic binder.

A blood sample applied to the porous spreading layer is uniformly spread within the spreading layer and, when a hydrophilic binder layer is employed, it simultaneously permeates into the binder layer. The binder layer has essentially semipermeable properties, and hence water and low molecular weight compounds diffuse and permeate into the binder layer while particles such as erythrocytes, leukocytes, thrombocytes, etc. do not permeate into the binder layer but are uniformly spread into the porous spreading layer and at the interface between the porous spreading layer and the binder layer. High molecular weight compounds such as albumin and globulin penetrate or do not penetrate into the binder layer depending upon the molecular weight and crystallinity of the binder polymer constituting the binder layer matrix.

Suitable hydrophobic binders which can be used for the binder layer, include thermoplastic resins such as polyvinyl acetate, polystyrene, polymethyl methacrylate, vinyl chloride-vinyl acetate copolymers, cellulose esters, etc. and the thermosetting resins such as polyurethanes, melamine, etc.

Suitable hydrophilic binders which can be used for the binder layer, include a wide variety of materials such as natural high molecular weight materials (e.g., gelatin, agarose, dextran, etc.) and hydrophilic synthetic high molecular weight materials (e.g., polyvinyl alcohol, polyacrylamide, polyacrylic acid, etc.). Of these, gelatin for photographic use is most preferred due to its excellent swelling properties for water, gel-forming capability, adhesion properties, water-absorbing properties, etc. and easy producibility.

Various additives may be added to the binder layer for the purpose of stabilizing the hue of hemoglobin and preventing penetration, diffusion, or precipitation of hemoglobin, as well as controlling spreading. Illustrative additives include low molecular weight or high molecular weight materials such as nonionic, cationic, or anionic surfactants, plasticizers, inorganic salts, organic acid salts, pH buffers, pigments, dyes, solid fine particulate fibers, oxidizing agents, reducing agents, acids, alkalis, etc. For the purpose of facilitating readout of the diameter of the spread circle, a pH indicator which becomes colored or discolored depending upon the pH of the blood serum, or a color reagent which reacts with a blood serum ingredient such as albumin to produce a color such as Bromocresol Green can be used.

The binder layer may in some cases be formed by two or more sub-layers for the purpose of improving adhesiveness and ease of readout and preventing curling. The thickness of the binder layer can range from about 0.1 μm to 1 mm, preferably from 1 μm to 100 μm, particularly preferably from 5 μm to 50 μm.

The HCT-determining sheet of the present invention can also be used in a process of determining HCT by merely measuring the diameter of the spread circle of blood formed by applying a drop of blood onto a porous spreading layer of the sheet.

This process is based on the principle that the hydrophilic porous spreading layer is greatly dependent, in its blood-spreading properties, upon the viscosity of the sample, or the content of particulate ingredients in the blood. Thus, this porous spreading layer has different characteristics from that of the above described spreading layer used in multi-layered integral analytical elements for chemically analyzing blood and described in Japanese patent application (OPI) Nos. 53,888/74 (corresponding to U.S. Pat. No. 3,922,158) and 131,786/77 (corresponding to U.S. Pat. No. 4,050,898) and Japanese patent application No. 72,047/79 (corresponding to U.S. patent application Ser. No. 157,737, filed June 9, 1980). That is, the spreading layer used in the multi-layered integral analytical elements must possess the above-described characteristics such that, when a definite amount of liquid is applied onto the sheet, a definite liquid-spread area results so that quantitative analysis can be conducted. In this case, the liquid-spread area must be definite even when the vicosity of the sample to be analyzed somewhat varies, and various means are incorporated therein to attain such characteristics.

On the other hand, the hydrophilic porous spreading layer used in the HCT-determining sheet of the present invention is such that the ease with which blood spreads is directly dependent upon the viscosity of the blood. That is, the porous spreading layer has characteristics such that blood with a low viscosity, i.e., blood with low HCT, forms a spread circle with a larger diameter due to the greater ease with which the blood spreads, whereas blood with a high viscosity, i.e., blood with high HCT, forms a spread circle with a smaller diameter due to the lesser ease with which the blood spreads. This means that the diameter of the spread circle and the viscosity of blood, or hematocrit value, are directly related to a negative proportional constant. In determining HCT using the HCT-determining sheet of the present invention, the relation between the diameter of the spread circle (or the area of the spread circle) and HCT is previously obtained by using a definite amount of standard blood, thus preparing a conversion table or a calibration curve. The HCT of an unknown blood sample can be determined simply by applying the sample to the porous spreading layer in the same amount as used in preparing the conversion table or the calibration curve, and measuring the diameter or the area of the spread circle.

The HCT-determining sheet of the present invention has another important advantage in that HCT can be determined without accurately weighing a blood sample. Blood is composed of a hemocyte component and a blood serum component and, when applied onto the surface of the porous spreading layer of the HCT-determining sheet in accordance with the present invention, double circles are formed as a result of spreading, with the inside circle containing the hemocyte component and the outside circle comprising the blood serum component alone. It has now been found that the ratio of diameter or area of the inside circle to that of the outside circle is in a definite relation with the HCT of an applied blood sample. Thus, HCT can be determined without accurately weighing a blood sample, by previously measuring the ratio of diameter or area of the inside circle to that of the outside circle and preparing a calibration curve of HCT versus the diameter or area ratio similarly with the above-described method of spreading a definite amount of sample to measure the diameters of outside and inside spread circles.

The present invention is described in more detail by the following non-limiting examples of the present invention.

EXAMPLE 1

A. Preparation of HCT-Determining Sheet

A solution containing 0.2% polyoxyethylene nonylphenoxy ether (nonionic surfactant, HS210, made by Nippon Oils & Fats Co., Ltd.) and 10% gelatin was coated on a 185-μm thick transparent polyethylene terephthalate (PET) film subbed with gelatin to thereby form a binder layer of a dry thickness of 15 μm composed of gelatin. This coated layer was swollen with water, and Microfilter FM-120 (a trademark for cellulose triacetate manufactured by Fuji Photo Film Co., Ltd.) of a mean pore size of 1.2 μm containing 0.5% (by weight) surfactant, HS210, was press-laminated thereon to prepare an HCT-determining sheet.

B. Preparation of Blood Samples

A fresh ACD preserved blood (preserved blood containing as preserving agents sodium citrate, citric acid and dextrose) was centrifuged to separate such into a hemocyte component and a blood serum component. Then, they were mixed with each other in various ratios to prepare samples. The HCT of each of the thus prepared samples was measured using an AMCO centrigue (E-24) and a capillary hematocrit tube. Thus, standard samples having an HCT of from 0 to 70% were obtained.

C. Measurement

Figure 5:
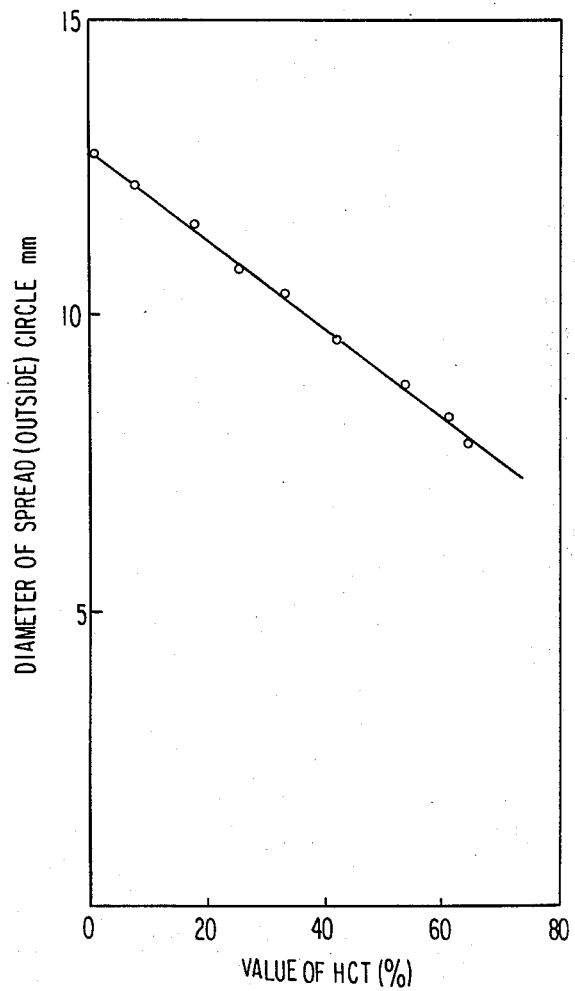
FIG. 5 is a graph showing the relationship between HCT determined in Example 1(C), and the diameter of the spread (outside) circle.

The HCT-determining sheet prepared in (A) above was cut into 30×30 mm squares. 10 μl of each blood sample of 0 to 70% in HCT prepared in (B) was taken up in a micropipet and applied to the square of HCT-determining sheet. 30 seconds after the application, double circles resulted, with the inside circle containing erythrocytes and the outside circle comprising blood serum. The outside diameter of each circle was measured from the side opposite the sample-applied side, i.e., from the side of the transparent PET film. The diameter of the outside circle and the HCT obtained in (C) were confirmed to be in such a relation that the diameter of the (outside) spread circle was in a direct relation with the HCT, with a negative proportional constant, as shown in FIG. 5.

EXAMPLE 2

A drop (about 20 μl) of each blood sample of 7 to 61% in HCT prepared in Example 1, (B), was applied to a 30×30 mm square of HCT-determining sheet prepared as described in Example 1, (A). 30 seconds after the application, the diameter of the inside circle containing erythrocytes and the diameter of the outside circle comprising blood serum were measured to determine the ratio. Thus, the results shown in Table 1 below were obtained. Table 1 shows that the ratio of inside circle/outside circle in diameter is linearly related with HCT.

TABLE 1

| | HCT (%) | | | | | |
|---|---|---|---|---|---|---|
| | 7 | 16 | 27 | 38 | 44 | 61 |
| Spread Circle Inside Diameter/ Outside Diameter | 0.33 | 0.41 | 0.48 | 0.56 | 0.58 | 0.67 |

EXAMPLE 3

Onto a porous spreading layer of HCT-determining sheet produced as described in Example 1 was applied 10 μl of fresh blood taken from a human vein using heparin as an anticoagulant. 30 seconds after the application, the diameter of the outside spread circle was measured to be 9.5 mm. The HCT was determined to be 43% from the calibration curve shown in FIG. 5.

On the other hand, the HCT of the same blood sample was determined according to the centrifugation method using a hematocrit tube in the same manner as in Example 1, (B). Thus, the HCT has determined to be 43%.

This showed that the HCT determined by using the HCT-determining sheet of the present invention agreed well with the HCT determined according to the conventional centrifugation method using a hematocrit tube.

EXAMPLE 4

Onto a 18-mm wide commercially available adhesive tape (made by Nitto Electric Industrial Co., Ltd.) comprising a 100 μm thick transparent PET film having coated thereon a pressure sensitive adhesive composition was press-laminated a micro-filter (FM-80, made by Fuji Photo Film Co., Ltd.) of 0.8 μm in mean pore size which had been rendered hydrophilic by impregnation with 0.2% alkylphenoxy polyethoxyethanol (non-ionic surfactant, Triton X-405, made by Rohm and Haas) to thereby prepare an HCT-determining sheet.

A drop of each of the standard blood samples prepared in Example 1, (B), was applied to this sheet to measure the diameter of the spread outside circle. A linear relationship was observed between the HCT determined according to the conventional contrifugation method and the diameter of the spread circle.

While the invention has been described in detail and with reference to specific embodiments thereof, it will be apparent to one skilled in the art that various changes and modifications can be made therein without departing from the spirit and scope thereof.

What is claimed is:

1. A hematocrit value determining element comprising a water-impermeable planar support having integrally provided thereon a porous spreading layer which has a hydrophilic surface and in which the surface of the internal voids or the interior is hydrophilic and water-insoluble, said porous spreading layer being such that blood spreads therethrough depending upon the spreading nature of the blood, wherein the porous spreading layer has a mean pore diameter ranging from about 0.1 μm to about 2.5 μm and wherein the porous spreading layer comprises a layer of a non-fibrous porous material or a fibrous porous material which has a yarn number count of about 100 to about 200.

2. The hematocrit value determining element as claimed in claim 1, wherein the hydrophilic porous spreading layer is water-insoluble.

3. The hematocrit value determining element as claimed in claim 1, wherein said water-impermeable planar support is transparent.

4. The hematocrit value determining element as claimed in claim 1, wherein said water-impermeable planar support is a support of metal, wood, paper, glass or a synthetic resin film.

5. The hematocrit value determining element as claimed in claim 1, wherein said mean pore diameter is from about 0.4 μm to about 2 μm and said yarn number count is about 120 to about 160.

6. The hematocrit value determining element as claimed in claim 1, wherein the hydrophilic porous spreading layer comprises a layer of a non-fibrous porous material or a fibrous porous material.

7. The hematocrit value determining element as claimed in claim 6, wherein the non-fibrous porous material comprises a porous membrane.

8. The hematocrit value determining element as claimed in claim 6, wherein said fibrous porous material is glass fiber, a fabric or paper.

9. The hematocrit value determining element as claimed in claim 1, which consists essentially of said water-impermeable planar support and said porous spreading layer.

10. The hematocrit value determining element as claimed in claim 9, wherein said porous spreading layer further contains at least one member selected from the group consisting of a pH buffer, an anticoagulant, an antihemolytic agent, an antioxidant, an oxidizing agent and an erythrocyte membrane-modifying agent.

11. The hematocrit value determining element as claimed in claim 10, wherein said erythrocyte membrane-modifying agent is selected from the groups consisting of a dye, a pigment, an inorganic salt, an aldehyde, an isocyanate and hydrogen peroxide.

12. The hematocrit value determining element as claimed in claim 1, wherein a binder layer is provided between said planar support and said porous spreading layer.

13. The hematocrit value determining element as claimed in claim 12, wherein said binder layer is a layer of a hydrophilic binder.

14. The hematocrit value determining element as claimed in claim 12, wherein said binder layer uniformly adheres the porous layer to the support in a fluid contact state and controls the spreading of a blood sample through the porous spreading layer.

15. The hematocrit value determining element as claimed in claim 12, wherein said binder layer contains a pH indicator which becomes colored or discolored depending upon the pH of blood serum or a color reagent which reacts with a blood serum ingredient to produce a color.

16. The hematocrit value determining element of claim 12, wherein said binder layer is formed of a hydrophobic binder or a hydrophilic binder selected from the group consisting of polyvinyl acetate, polystyrene, polymethyl methacrylate, vinyl chloride-vinyl acetate copolymers, cellulose esters, polyurethanes, melamine, gelatin, agarose, dextran, polyvinyl alcohol, polyacrylamide and polyacrylic acid.

17. The hematocrit value determining element as claimed in claim 16, wherein said binder layer contains at least one additive selected from the group consisting of nonionic, cationic or anionic surfactants, plasticizers, inorganic salts, organic acid salts, pH buffers, pigments, dyes, solid fine particulate fibers, oxidizing agents, reducing agents, acids and alkalis.

* * * * *